United States Patent [19]

Grau

[11] Patent Number: 4,608,364

[45] Date of Patent: Aug. 26, 1986

[54] PHARMACEUTICAL AGENT FOR THE TREATMENT OF DIABETES MELLITUS

[75] Inventor: Ulrich Grau, Hofheim am Taunus, Fed. Rep. of Germany

[73] Assignee: Hoechst Aktiengesellschaft, Fed. Rep. of Germany

[21] Appl. No.: 632,859

[22] Filed: Jul. 20, 1984

[30] Foreign Application Priority Data

Jul. 22, 1983 [DE] Fed. Rep. of Germany ....... 3326473

[51] Int. Cl.$^4$ ............................................. A61K 37/26
[52] U.S. Cl. .......................................... 514/4; 514/3; 514/866
[58] Field of Search ...................... 514/4, 3; 260/112.7

[56] References Cited

FOREIGN PATENT DOCUMENTS 2104381  3/1983  United Kingdom .................... 514/4

*Primary Examiner*—Frederick E. Waddell
*Attorney, Agent, or Firm*—Finnegan, Henderson, Farabow, Garrett & Dunner

[57] ABSTRACT

The invention relates to medicaments consisting of a physiologically acceptable excipient and an active compound combination of
(a) an insulin derivative of the formula I

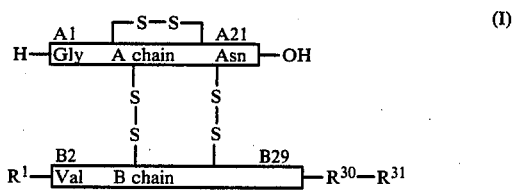

in which $R^1$ denotes H or H—Phe, $R^{30}$ represents the radical of a neutral L-aminoacid and $R^{31}$ represents a physiologically acceptable organic group of basic character with up to 50 carbon atoms, with an isoelectric point between 5.8 and 8.5, and
(b) an insulin of the formula I in which $R^1$ denotes H or H—Phe, $R^{30}$ represents Ala, Thr or Ser and $R^{31}$ denotes OH,
and to its use for the treatment of diabetes mellitus.

19 Claims, No Drawings

PHARMACEUTICAL AGENT FOR THE TREATMENT OF DIABETES MELLITUS

Diabetes mellitus is a metabolism disorder which exhibits an increased level of blood sugar as the essential symptom. It is caused by an insufficient amount of the pancreatic hormone insulin being released. At present, the natural hormone is as a rule replaced by animal insulin isolated from the glands of slaughtered animals, or human insulin, which is accessible semisynthetically from porcine insulin or by genetic engineering methods.

Two fundamentally different ways have hitherto been taken in the use of genetic engineering methods: separate synthesis of A and B chains and their subsequent chemical recombination, and synthesis of preproinsulin, the naturally occurring precursor of insulin. In the proinsulin molecule, the A and B chain are linked by a connecting piece, the C peptide. According to current theory, the most important function of this piece is spatial fixing of the two chains relative to one another, so that correct folding can take place. When folding has taken place, the three disulfide bridges are linked and the unmodified three-dimensional structure of the insulin is thus stabilized. The C peptide is split off by enzymes having a tryptic and carboxypeptidase B activity. The splitting sites are predetermined by a Lys-Arg sequence (before the N-terminus of the A chain) or an Arg-Arg sequence (at the C-terminus of the B chain). Only free insulin has full biological activity, because part of the biological recognition region on the surface of the molecule is probably masked in the presence of the C peptide.

The particular chemical nature of insulin means that therapy is as a rule parenteral; the hormone would be completely degraded even before it was able to act, for example, on passage through the stomach and intestine. However, degradation reactions, essentially by various, relatively non-specific proteolytic enzymes, also take place at the injection site and in the circulation. The short in vivo half life of only about 7 minutes which thereby results is in principle appropriate from the physiological point of view in the context of homeostatis; however, therapy is thereby made considerably more difficult, because the diabetic must typically inject himself four times daily, as a rule shortly before mealtimes.

Early attempts have accordingly already been made to impart a protracted action to the insulin. The most successful so far have been those methods in which the insulin is converted into a sparingly soluble state by addition of a depot auxiliary. Depot auxiliaries include, above all, divalent zinc ions, in the presence of which the insulin can be in crystalline or amorphous form in a neutral medium. The addition of basic proteins, for example protamine sulfate or human globin, has the same effect, since insulin is an acid molecule with an isoelectric point $p_I$ of 5.4: basic protein and insulin are in the form of a crystalline or amorphous salt-like, sparingly soluble complex in the neutral range.

It is imagined that the slow release of the insulin from these sustained release formulations takes place by dilution, i.e. diffusion, of individual components which build up the crystal or the amorphous precipitate, or, in the case of insulin complexes with basic proteins, by proteolytic degradation of the depot excipient.

Human proinsulin, either by itself or in combination with the customary depot additives, has recently also been discussed as a delayed action principle (see German Pat. No. A 3,232,036). The theory is that the proteolytic splitting of the C peptide is delayed in vivo and hence the fully active hormone is released from the proinsulin, which has only little inherent biological activity (about $\frac{1}{8}$ of the activity of insulin, based on the amount of protein). Only those proinsulins which are identical (there are evidently several) or very similar in their sequence to that from humans are acceptable for use on humans. As is generally known, porcine and bovine proinsulin are immunogenic. The exact mode of action of proinsulin, however, is at present still open. It has in no way been proved that insulin is specifically released. On the contrary, degradation in vivo will take place in several ways, with production of in most cases inactive fragments. The therapeutic use of pro-insulin could thus rather be found, if at all, at the receptor level.

Diabetes therapy is characterized by individual influence factors, such as differences in the utilizability of the meals, differences in the characteristics of the subcutaneous tissue and also specific eating habits, physical activities and many others besides. It is thus absolutely essential for good adjustment of the blood sugar to have available a number of insulin products with different action characteristics which are adapted to the individual requirements. In connection with non-optimum adjustment, in particular the topic of delayed diabetic damage is discussed, besides the immediate subjective and objective effects, such as hyper- or hypoglycemia. This delayed damage includes, above all, macro- and micro-angiopathy, neuropathy, nephropathy and retinopathy.

Besides pure delayed action insulins, so-called intermediate acting insulins have above all proved to be preparations which are optimally suited to the requirements of the patient. These are mixtures of a delayed action component and a component having an immediate and short action. Such mixtures are in general complicated multiphase systems which remain stable over a long period only when mixed in relatively narrowly defined proportions. Thus, for example, a suspension of 2-zinc-insulin crystals from pigs is not freely miscible with dissolved porcine insulin. The admixed, dissolved insulin precipitates immediately or in the course of time because of the relatively high zinc content which is necessary to stabilize the crystals. Such mixtures are stable within narrow limits if bovine insulin (but in this case the specious purity, a medically desirable property, is lost) or a mixture of dissolved porcine insulin and phenylalanine (B1)-porcine insulin is used as the dissolved insulin (German Pat. No. A 2,418,218 and German Pat. No. A-2,459,515). From the point of view of miscibility with dissolved insulin, protamine-insulin formulations are more advantageous, if crystals of protamine and insulin are used in an isophane ratio as the delayed action component. NPH-typical action profiles can be produced with these products; the presence of protamine sulfate, as an exogenous but relatively acceptable protein, appears a suitable additive.

The object of the invention is to provide a stable pharmaceutical agent which has an action characteristic adapted to the individual requirements of the diabetic.

According to the invention, this object has now been achieved by an active compound combination of an insulin derivative, the B chain of which carries a C-terminal organic group of basic character, and an unmodified insulin or its des-Phe$^{B31}$ analog.

Insulin derivatives which carry Arg—OH or Arg—Arg—OH radicals on the C-terminal end of the B chain have already been described. As is known, these derivatives are formed as natural intermediates on enzymatic conversion of proinsulin into insulin in vivo, and small amounts can also be detected in pancreas extracts. The radicals mentioned are usually split off by trypsin and/or carboxypeptidase B or enzymes of similar specificity, unmodified insulin being released.

More of these insulin derivatives which are basemodified on the C-terminal end, processes for their preparation and their use are the subject of copending U.S. patent application Ser. No. 632,845 filed concurrently herewith.

The invention relates to medicaments consisting of a physiologically acceptable excipient and an active compound combination, which contain, as the active compound combination, (a) an insulin derivative of the formula I

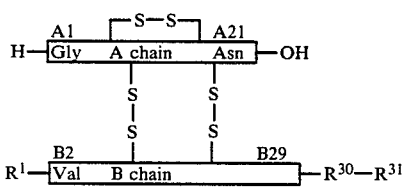

in which
R$^1$ denotes H or H—Phe,
R$^{30}$ represents the radical of a neutral L-amino-acid which can be genetically coded and
R$^{31}$ represents a physiologically acceptable organic group of basic character with up to 50 carbon atoms, in the build-up of which 0 to 3 α-aminoacids participate and in which the terminal carboxyl function optionally present can be free, as an ester function, as an amide function, as a lactone or reduced to CH$_2$OH,
with an isoelectric point between 5.8 and 8.5, and
(b) an insulin of the formula I in which
R$^1$ denotes H or H—Phe,
R$^{30}$ represents Ala, Thr or Ser and
R$^{31}$ denotes OH,
or physiologically acceptable salts thereof, and, if appropriate, proinsulin and, if appropriate, C peptide.

Preferred agents are those in which, in the insulin derivative of the formula I, mentioned under (a), R$^{31}$ represents a radical of the formula —X$_n$—S, in which
n is 0, 1, 2 or 3,
X represents identical or different radicals of naturally occurring neutral or basic L-amino-acids (preferably a basic L-aminoacid, in particular Arg, Lys, His or Orn) and/or of D-amino-acids corresponding to these, and
S denotes OH or a physiologically acceptable group which blocks the carboxyl group and which, if n is 0, carries a positively charged or protonatable basic radical or, if n is greater than 0, can carry such a radical, and in which the C-terminus —X—S can also represent the radical of an amino-acid reduced to the corresponding alcohol or, if n is 2 or 3, can represent the homoserine-lactone radical.

Particularly preferred insulin derivatives of the formula I are those which carry phenylalanine in position B1. Those which contain Ala, Thr or Ser in position B30 are also preferred. Their A chain and the (B2-29) chain advantageously have the sequences of bovine or porcine insulin or, in particular, those of human insulin.

The aminoacid radicals X and radicals of the corresponding derivatives can be in the D- or L-configuration independently of one another. However, the L-configuration is preferred for all the radicals.

The following L-aminoacids can be genetically coded: Gly, Ala, Ser, Thr, Val, Leu, Ile, Asp, Asn, Glu, Gln, Cys, Met, Arg, Lys, His, Tyr, Phe, Trp and Pro (neutral aminoacids are underlined).

A neutral, naturally occurring aminoacid is understood as meaning, in particular, Gly, Ala, Ser, Thr, Val, Leu, Ile, Asn, Gln, Cys, Met, Tyr, Phe, Pro or Hyp. A basic, naturally occurring aminoacid is understood as meaning, in particular, Arg, Lys, Hyl, Orn, Cit or His.

Groups which may block a free carboxyl function on the C-terminal end of the B chain in the insulin derivatives according to the invention are understood as meaning, above all, ester and amide groups, preferably (C$_1$ to C$_6$)-alkoxy, (C$_3$ to C$_6$)-cycloalkoxy, NH$_2$, (C$_1$ to C$_6$)-alkylamino or di-(C$_1$ to C$_6$)-alkylamino, or basic groups, such as amino-(C$_2$ to C$_6$)-alkoxy, (C$_2$ to C$_4$)-alkylamino-(C$_2$ to C$_4$)-alkoxy, di-(C$_1$ to C$_4$)-alkylamino-(C$_2$ to C$_6$)-alkoxy, tri-(C$_1$ to C$_4$)-alkylammonio-(C$_2$ to C$_6$)-alkoxy, amino-(C$_2$ to C$_6$)-alkylamino, (C$_1$ to C$_4$)-alkylamino-(C$_2$ to C$_6$)-alkylamino, [di-(C$_1$ to C$_4$)-alkylamino](C$_2$ to C$_6$)alkylamino or [tri-(C$_1$ to C$_4$)-alkylammonio]-(C$_2$ to C$_6$)-alkylamino, in particular —O—(CH$_2$)$_p$—NR$_2$, —O—(CH$_2$)$_p$—N$^\oplus$R$_3$ —NH—(CH$_2$)$_p$—NR$_2$ or —NH—(CH$_2$)$_p$—N$^\oplus$R$_3$, in which p is 2 to 6 and the radicals R are identical or different and represent hydrogen or (C$_1$ to C$_4$)-alkyl.

The following compounds may be mentioned as examples from the series of insulin derivatives of the formula I, according to the invention, without limiting the invention to these compounds:
Human insulin-Arg$^{B31}$—OH
Porcine insulin-Arg$^{B31}$—OH
Bovine insulin-Arg$^{B31}$—OH
Human insulin-Arg$^{B31}$—Arg$^{B32}$—OH
Porcine insulin-Arg$^{B31}$—Arg$^{B32}$—OH
Bovine insulin-Arg$^{B31}$—Arg$^{B32}$—OH
Des—Phe$^{B1}$-porcine insulin-Arg$^{B31}$—OH
Des—Phe$^{B1}$-human insulin-Arg$^{B31}$—OH
Des—Phe$^{B1}$-porcine insulin-Arg$^{B31}$—Arg$^{B32}$—OH
Des—Phe$^{B1}$-human insulin-Arg$^{B31}$—Arg$^{B32}$—OH
Porcine insulin-Arg$^{B31}$—OCH$_3$
Human insulin-Arg$^{B31}$—OCH$_3$
Bovine insulin-Arg$^{B31}$—OCH$_3$
Porcine insulin-Arg$^{B31}$—Arg$^{B32}$—OCH$_3$
Human insulin-Arg$^{B31}$—Arg$^{B32}$—OCH$_3$
Des—Thr$^{B30}$-human insulin-Val$^{B30}$—Arg$^{B32}$—OCH$_3$
Des—Thr$^{B30}$-human insulin-Val$^{B30}$—Arg$^{B31}$—OH
Des—Thr$^{B30}$-human insulin-Val$^{B30}$—Ala$^{B31}$—Arg$^{B32}$—OH
Human insulin-Lys$^{B31}$—OH
Human insulin-D—Arg$^{B31}$—OH
Human insulin-D—Arg$^{B31}$—Arg$^{B32}$—OH
Human insulin-Arg$^{B31}$—D—Arg$^{B32}$—OH
Human insulin-Lys$^{B31}$—Arg$^{B32}$—OH
Human insulin-Arg$^{B31}$—Lys$^{B32}$—OH
Human insulin-Argininol$^{B31}$
Human insulin-Val$^{B31}$—Arg$^{B32}$—OH
Human insulin-Val$^{B31}$—Arg$^{B32}$—Arg$^{B33}$—OH
Human insulin-Arg$^{B31}$-Argininol$^{B32}$
Human insulin-Lys$^{B31}$—Arg$^{B32}$—Arg$^{B33}$—OH

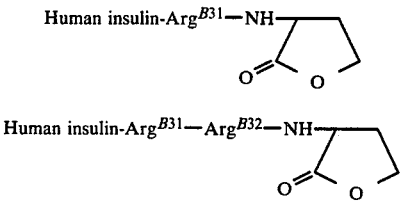

Human insulin-Arg$^{B31}$—NH—

Human insulin-Arg$^{B31}$—Arg$^{B32}$—NH—

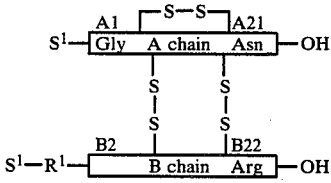

Human insulin-Arg$^{B31}$—NH$_2$
Human insulin-Arg$^{B31}$—Arg$^{B32}$—NH$_2$
Human insulin-Orn$^{B31}$—OH
Human insulin-Leu$^{B31}$—Cit$^{B32}$—OH
Human insulin-(B30)—OCH$_2$CH$_2$—NH$_2$
Human insulin-(B30)—NH—CH$_2$CH$_2$—NH$_2$
Human insulin-Arg$^{B31}$—O—CH$_2$—CH$_2$—NH$_2$
Human insulin-Arg$^{831}$—NH—CH$_2$—CH$_2$—N(CH$_3$)$_2$
Human insulin-(B30)—O—CH$_2$—$\oplus$N(CH$_3$)$_3$
Human insulin-(B30)—NH—CH$_2$—CH$_2$—$\oplus$N(CH)$_3$
Human insulin-Leu$^{B31}$—O—CH$_2$—CH$_2$—CH$_2$—$\oplus$N(C$_2$H$_5$)$_3$
Human insulin-Trp$^{B31}$—Trp$^{B32}$-Trp$^{B33}$—NH(CH$_2$)$_6$—N$^{61}$ (nC$_4$H$_9$)$_3$.

The insulin derivatives of the formula I are prepared by a process which comprises (a) condensing a des-octapeptide-(B23-30)-insulin of the formula II

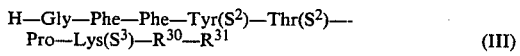

(II)

in which R$^1$ denotes Phe or a bond and S$^1$ denotes an amino-protective group which can be split off by proton solvolysis or by β-elimination, such as the tert.-butoxycarbonyl (Boc), the tert.-amyloxycarbonyl (Aoc) or the methylsulfonylethoxycarbonyl (Msc) radical, with a peptide of the formula III H—Gly—Phe—Phe—Tyr(S$^2$)—Thr(S$^2$)—Pro—Lys(S$^3$)—R$^{30}$—R$^{31}$ (III)

in which R$^{30}$ and R$^{31}$ have the meanings defined above, S$^2$ represents hydrogen, Bzl or Bu$^t$ and S$^3$ represents a urethane-protective group, such as Boc, Moc or Z, any free COOH, OH, SH, ω—NH$_2$, guanidino and/or imidazole groups present on the radicals R$^{30}$ and R$^{31}$ being protected, if necessary, in a manner which is known per se, and, if appropriate, splitting off the protective groups present in a manner which is known per se, (b) reacting, in the presence of trypsin or a trypsin-like endo-peptidase, a des-B30-insulin of the formula I in which R$^1$ represents H or H—Phe and the C-terminus R$^{30}$—R$^{31}$ together represents OH, with a compound of the formula IV

H—R$^{30}$—R$^{31}$ (IV)

in which R$^{30}$ and R$^{31}$ have the meanings defined above and in which the free COOH, OH, SH, ω—NH$_2$, guanidino and/or imidazole functions present are protected, if necessary, in a manner which is known per se, and, if appropriate, subsequently splitting off the protective groups present in a manner which is known per se, or (c) for the preparation of an insulin derivative with aminoacid radicals in the radical R$^{31}$ in the L-configuration, chemically and/or enzymatically splitting a proinsulin, proinsulin analog or preproinsulin analog or an intermediate of these compounds.

The des-B30-insulins used as starting compounds in process variant (b) are known, for example from European Pat. No. A-46,979 or Hoppe-Seyler's Z.Physiol. Chem. 359 (1978) 799. The starting material of the formula IV used in variant (b) is prepared in a manner which is known per se by the methods of peptide chemistry. Protective groups which can be used for IV are described in detail in M. Bodanzky et al., Peptide Synthesis, 2nd Edition, 1976, Wiley & Sons.

Human or primate proinsulin is meanwhile accessible as the starting material for process variant (c) by genetic engineering methods: the derivatives Arg(B31) and di-Arg(B31-32) are accessible therefrom by simple digestion with trypsin or trypsin-like enzymes. However, it is also possible additionally to construct relatively simple plasmids which lead to novel insulin derivatives because they code other neutral or basic aminoacids instead of the arginines naturally occurring on B31 or B32.

The preparation of proinsulin using recombinant DNA methodology requires the formation of a DNA sequence which codes the aminoacid sequence of a proinsulin, which can be achieved either by isolation or construction or by a combination of the two. The proinsulin DNA is then inserted into a suitable cloning and expression carrier in the reading phase. The carrier serves to transform a suitable microorganism, and the transformed microorganism thereby obtained is then subjected to fermentation conditions which lead to the formation of further copies of the proinsulin-containing vector and to the expression of the proinsulin of a proinsulin derivative or a proinsulin precursor or a preproinsulin derivative.

If the expression product is a proinsulin precursor, such a product in general contains the proinsulin aminoacid sequence bound at its terminal amino group to a fragment of a protein which is usually expressed by the gene sequence into which the proinsulin or proinsulin derivative has been inserted. The proinsulin aminoacid sequence is bound to the protein fragment via a site which can be split specifically, which is, for example, methionine.

The resulting proinsulin aminoacid sequence is split off from the fused gene product, for example as described in German Pat. No. A-3,232,036, and, after purification, the proinsulin is isolated.

The enzymatic splitting of the proinsulin or proinsulin derivative obtained in this manner is effected by a procedure analogous to that described in Excerpta Medica International Congress Series No. 231, page 292 et seq., or that in German Patent Application No. P 3,209,184 (HOE 82/F 047).

In addition to the known arginine(B30) and diarginine(B31-32) derivatives and those derivatives which are accessible by genetic engineering methods and carry naturally occurring L-aminoacids on R$^{31}$, a number of novel insulin derivatives which have, as a characteristic, one or more basic groups and/or the absence of the free carboxyl group, so that the net charge of the molecule increases by at least one positive charge in comparison with unmodified insulin or in comparison with des-Phe$^{B1}$-insulin, are thus accessible with the aid of the semi-synthetic processes described.

These derivatives include, for example, derivatives which contain at position B-31, instead of the naturally occurring aminoacid L-lysine, L-histidine or L-arginine, their D-enantiomers of the usual D- or L-aminoacid analogs, which carry a basic grouping (for example ornithine or hydroxylysine) in the side chain. Instead of an aminoacid, the choline ester group, for example, may occur at the site of position B31, which means that two net positive charges are obtained. The aminoacid or aminoacid analog at position B31 can have a free carboxyl end or be esterfied with simple alcohols (for example methanol or ethanol) or amidated with simple nitrogen bases (for example ammonia or mono- or dimethylamine); it can also be esterfied, for example, with choline. A neutral or another naturally occurring basic aminoacid or one of the aminoacid derivatives described above, for example, can follow at position B31; in an analogous manner, like carboxyl group thereof can be free or esterified or amidated. In this case also, the choline ester group or another neutral or basic aminoacid or an aminoacid analog, for example, can follow.

All these insulin derivatives have the common factor that the additional positive charge(s) on the surface of the molecule gives to the molecule an isoelectric point which is shifted into the neutral range. Depending on the derivative, isoelectric points of 5.8 to 8.5, in particular 6.2 to 8.2, are measured on isoelectric focusing. The derivatives are thus less soluble in the neutral range than unmodified insulin or proinsulin, which have their isoelectric point and hence their region of maximum insolubility at pH 5.4, whilst they are usually in solution in the neutral range.

These insulin derivatives of the formula I are accordingly completely novel delayed action principles in which the action can be started without depot auxiliaries, such as zinc or protamine sulfate. The depot action is attributed to an inherent physical principle resulting from protein chemistry, i.e. the sparing solubility at the isoelectric point. Redissolving under physiological conditions, as will be assumed, should be achieved by splitting off the additional basic groups, which is brought about, depending on the derivative, by tryptic or trypsin-like, and/or carboxypeptidase B or carboxypeptidase B-like and/or esterase activity. The particular groups split off are either purely physiological metabolites, such as aminoacids, ornithine or cholone, or physiologically acceptable substances which can easily be metabolized.

Porcine insulin-Arg$^{B31}$—OH and the corresponding diarginine derivative have only 62% and, respectively, 66% of the activity of unmodified porcine insulin, according to the investigations by Chance, Excerpta Medica International Congress Series No. 231, pages 292 and 293.

Surprisingly, it has now been found that (also in contrast to proinsulin) the biological activity of the derivatives is of about the same level as that of unmodified insulin. Also in contrast to the intermediates described in the literature, which still contain parts of the heterologous C peptide, their immunogenic action is no more powerful than that of the corresponding insulin itself. The abovementioned values of Chance, which are too low, are possibly caused by the fact that these peptides were not in pure form or that the measurement had a systematic error.

Besides using the derivatives described, by themselves or as a mixture, as pure delayed action insulins or in combination with the known depot excipients, it is now possible to prepare, in many ways, stable mixtures with insulin which is rapidly available, for example with dissolved contents. A range of very finely adjusted action profiles is thus accessible.

Particularly suitable products are neutral mixtures of one or more derivatives, which act as sustained release components, with dissolved, unmodified insulin, preferably from the same species. In addition, however, it is also possible to use proinsulin and/or C peptides, in each case by itself or in combination with insulin, as the dissolved component. The characteristic of these formulations is that they are stable in all mixing ratios. This is a prerequisite for the preparation of the intermediately active insulin products which are today very common in therapy.

The agents according to the invention can also contain several different insulin derivatives of the formula I and/or several different insulins of the formula I. Moreover, other therapeutically interesting combinations can also be used, such as, for example, a mixture of derivative and insulin and/or proinsulin and/or des-Phe$^{B1}$-insulin and/or C peptide in dissolved form or in the form of NPH crystals or other conventional delayed action forms. In this manner, products having a very long action and with a different basal profile, inter alia, can be prepared. This would be desirable precisely with human insulin, since, from experience gained so far, its duration of action does not have a true ultra-sustained release profile, as is the case, for example, with the analogous bovine insulin products, either in the form of zinc crystals or in the form of NPH crystals.

The insulin and/or proinsulin and/or des-Phe$^{B1}$-insulin and/or C peptide and insulin derivative of the formula I can also be used in the form of an alkali metal salt or the ammonium salt.

The mixing proportions of unmodified insulin and/or proinsulin and/or des-Phe$^{B1}$-insulin and/or C peptide and insulin derivative can vary in the range from 0 to 99% of insulin, and 0 to 99% or proinsulin, and 0–99% of phenylalanine-(B1)-insulin, and 0–99% of C peptide and 1 to 100% of insulin derivative (based on the total amount of these peptides).

An acid solution, for example of the insulin derivative and insulin or proinsulin, which has a pH below the isoelectric point of the insulin is also a use form according to the invention.

Preferred agents have a pH value between 2.5 and 8.5 and are in solution or suspension.

The use forms described are typically dissolved or suspended in an aqueous medium which additionally contains a suitable isotonicity agent, for example glycerol or sodium chloride, and a suitable agent against microbial attack, for example phenol, m-cresol or p-hydroxybenzoic acid ester, in a suitable dosage. This physiologically acceptable excipient can additionally contain, in the pH range from 5.0 to 8.5, a buffer substance, for example sodium acetate, sodium citrate, sodium phosphate or tris-(hydroxymethyl)-aminomethane. Dilute acids, typically hydrochloric acid, or dilute alkalis, typically sodium hydroxide solution, are used for dissolving and for adjustment of the pH value.

The insulin content and/or proinsulin content and/or des-Phe$^{B1}$-insulin content and/or C peptide content and the content of the insulin derivative of the formula I can, independently of one another, in each case be in dissolved, amorphous and/or crystalline form. In each case any desired part of the insulin content and/or proinsulin content and/or des-Phe-insulin content and/or C peptide content and the content of the insulin derivative of the formula I can be in crystalline form, and in each case any other desired part of the insulin content and/or proinsulin content and/or des-Phe-insulin content and/or C peptide content and the content of the insulin derivative of the formula I can be in amorphous form, and in each case the remainder of the insulin content and/or proinsulin content and/or des-Phe-insulin content and/or C peptide content and of the content of the insulin derivative of the formula I can be in dissolved form.

The formulation can contain suitable amounts of auxiliaries with a delaying action (depot auxiliaries), such as, for example, protamine sulfate, globin or zinc (0 to 100 µg/100 I.U.).

This delayed action principle can be used in combination with the entire active compound content or parts thereof. The formulation can also contain several different auxiliaries having a delaying action.

It is sometimes advantageous to add to the formulation according to the invention a suitable amount of a suitable stabilizer which prevents precipitation of protein when the formulation is exposed to heat or mechanical stress on contact with various materials. Such stabilizers are known, for example, from European Pat. No. A-18,609, German Pat. No. A-3,240,177 or WO-83/00288.

The following examples serve to further illustrate the invention, without restricting the invention to these.

EXAMPLE 1

Insulin-Arg$^{B31}$—Arg$^{B32}$—OH from pigs, prepared by tryptic digestion from porcine proinsulin, in a neutral formulation with 40 IU/ml, and the miscibility thereof with 20% or 40% dissolved porcine insulin (40 IU/ml):

| | |
|---|---|
| Insulin-Arg$^{B31}$—Arg$^{B32}$—OH from pigs (27.0 IU/mg) | 14.8 mg |
| Sodium dihydrogen phosphate dihydrate | 21.0 mg |
| Glycerol | 160.0 mg |
| Phenol | 6.0 mg |
| m-Cresol | 15.0 mg | are dissolved in a total volume of 10 ml with water.

The pH is brought to 7.3 by addition of 1N HCl or 1N NaOH. A solution of porcine insulin containing 40 IU/ml in a similar medium or the same medium is mixed in, so that its amount by volume is 20% and 40%. The total content and the content in the supernatant liquor is determined with the aid of HPLC, in each case immediately and after storage at 4° C. for 3 months.

| | Total determination | | Supernatant Liquor | |
|---|---|---|---|---|
| | t = O | 3 months 4° C. | t = O | 3 months 4° C. |
| 20% | 40 IU/ml | 40 IU/ml | 7.5 IU/ml | 7.8 IU/ml |
| 40% | 40 IU/ml | 40 IU/ml | 16.2 IU/ml | 15.6 IU/ml |

Porcine insulin-Arg$^{B31}$—Arg$^{B32}$—OH is separated from porcine insulin by HPLC. No derivative can be detected in the supernatant liquor, i.e. the insoluble content is not dissolved. Conversely, after washing the precipitate, no insulin can be detected, i.e. insulin does not precipitate.

EXAMPLE 2

Porcine insulin-Arg$^{B31}$—OH, prepared by tryptic digestion from porcine proinsulin, mixed with 25% (activity) of dissolved porcine proinsulin in a neutral formulation with 40 IU/ml, and the depot action thereof:

| | |
|---|---|
| Porcine insulin-Arg$^{B31}$—OH 27.5 IU/mg | 10.9 mg |
| Porcine proinsulin 3.3 IU/mg | 30.3 mg |
| Sodium acetate | 14.0 mg |
| Methyl p-hydroxybenzoate | 10.0 mg |
| Sodium chloride | 80.0 mg | are mixed in a total volume of 10 ml with water.

The pH is brought to 7.0 by addition of 1N HCl or 1N NaOH.

Such a suspension exhibits a depot action in dogs, which is similar to a comparison depot product (Optisulin(®) Depot CS).

EXAMPLE 3

Porcine insulin-Arg$^{B31}$—Arg$^{B32}$—OH, prepared from porcine proinsulin by tryptic digestion, in the form of NPH crystals, mixed with 25% of des-phenylalanine-(B1)-porcine insulin, prepared from porcine insulin by Edman degradation, in a neutral formulation with 40 IU/ml, and the delayed action thereof:

| | |
|---|---|
| Porcine insulin-Arg$^{B31}$—Arg$^{B32}$—OH 27.0 IU/mg | 11.1 mg |
| des-Phenylalanine-(B1)-porcine insulin 28.0 IU/mg | 3.6 mg |
| Protamine sulfate | 1.0 mg |
| Sodium dihydrogen phosphate dihydrate | 21.0 mg |
| Phenol | 6.0 mg |
| m-Cresol | 16.0 mg |
| Glycerol | 160.0 mg | are mixed in a total volume of 10 ml with water.

The pH is brought to 7.3 by addition of 1N HCl or 1N NaOH.

Such a suspension exhibits a depot-like course of action in dogs.

EXAMPLE 4

Human insulin-(B30)-choline ester, prepared from porcine insulin by semi-synthesis, mixed with 40% of human insulin and 20% (by weight) of human C peptide, in a neutral formulation with 40 IU/ml, and the medium-duration action characteristics thereof:

| | |
|---|---|
| Human insulin-(B30)-choline ester (28 IU/mg) | 7.2 mg |
| Human insulin (28 IU/mg) | 7.2 mg |
| Human C peptide | 3.6 mg |
| Sodium dihydrogen phosphate dihydrate | 21.0 mg |
| m-Cresol | 27.0 mg |
| Glycerol | 160.0 mg | are mixed in a total volume of 10 ml with water.

The pH value is brought to 7.3 by addition of 1N HCl or 1N NaOH.

Such a suspension exhibits an action profile comparable with that of a combination product (for example Komb-H-Insulin(®), Hoechst), in dogs.

EXAMPLE 5

Human insulin-Arg$^{B31}$—Lys$^{B32}$—OCH$_3$, prepared by semi-synthesis from porcine insulin, mixed with 50% of zinc-human insulin crystals in a formulation with 40 IU/ml, and the delayed action thereof:

| | |
|---|---|
| Human insulin-Arg$^{B31}$—Lys$^{B32}$—OCH$_3$ (27.0 IU/mg) | 7.4 mg |
| Human insulin (28 IU/mg) | 7.4 mg |
| Zinc chloride, anhydrous | 0.23 mg |
| Sodium acetate | 14.0 mg |
| Methyl p-hydroxybenzoate | 10.0 mg |
| Sodium chloride | 80.0 mg | are mixed in a total volume of 10 ml with water.

The pH is brought to 7.0 by addition of 1N HCl or 1N NaOH.

Such a preparation has a pronounced sustained release action in rabbits (0.4 IU/kg).

EXAMPLE 6

Human insulin-Arg$^{B31}$—OH mixed with 30% of human insulin-Arg$^{B31}$—Arg$^{B32}$—OH, both prepared by tryptic digestion from primate proinsulin expressed in *E. coli*, mixed with 40% of crystalline NPH-human insulin in a formulation with 40 IU/ml, and the pronounced sustained release action thereof:

| | |
|---|---|
| Human insulin-Arg$^{B31}$—OH (27.5 IU/mg) | 4.4 mg |
| Human insulin-Arg$^{B31}$Arg$^{B32}$—OH (27.0 IU/mg) | 4.4 mg |
| Human insulin (28 IU/mg) | 5.7 mg |
| Protamine sulfate | 0.5 mg |
| Sodium dihydrogen phosphate dihydrate | 21.0 mg |
| m-Cresol | 15.0 mg |
| Phenol | 6.0 mg |
| Glycerol | 160.0 mg | are mixed in a total volume of 10 ml with water.

The pH is brought to 7.3 by addition of 1N NaOH or 1N HCl.

Such a suspension exhibits a markedly delayed and long-lasting action in rabbits.

I claim:

1. A pharmaceutical composition stable on storing and being suitable for the treatment of diabetes mellitus consisting of a physiologically acceptable excipient and an active compound combination, which contains, as the active compound combination,
   (a) an insulin derivative of the formula I

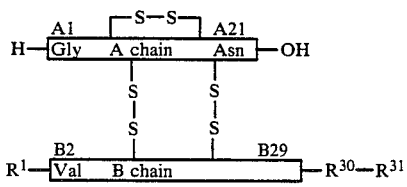

in which
R$^1$ denotes H or H—Phe

R$^{30}$ represents the radical of Ala, Thr or Ser and
R$^{31}$ represents a physiologically acceptable organic group of basic character of the formula X$_n$—S which has up to 50 carbon atoms, in which
  n is 0, 1, 2 or 3,
  X represents identical or different radicals of naturally occurring neutral or basic α-amino acids and
  S denotes OH or a physiologically acceptable group which blocks the carboxyl group but S being, if n is 0, a positively charged or protonatable basic radical or, if n is greater than 0, S can carry such a radical, or in which, if n is 2 or 3, the C-terminus X—S can also represent the homoserine-lapton radical
and which contains or does not contain a terminal carboxyl function or an ester or an amide thereof,
with an iso electric point between 5.8 and 8.5, and
(b) an insulin of the formula I in which R$^1$ denotes H or H—Phe, R$^{30}$ represents Ala, Thr or Ser and R$^{31}$ denotes OH, or
(b2) physiologically acceptable salts thereof, or
(b3) proinsulin or
(b4) C peptide or
(b5) a combination thereof, component (a) being present in an amount of at least 1% by weight.

2. A composition as claimed in claim 1, in which R$^1$ represents H—Phe in the insulin derivative and in the insulin of the formula I.

3. A composition as claimed in claim 1, in which the amino acid radicals X are in the L-configuration in the insulin derivative of the formula I, mentioned under (1a).

4. A composition as claimed in claim 1, in which S represents OH or (C$_1$ to C$_6$)-alkoxy.

5. A composition as claimed in claim 1, in which X denotes Lys or Arg or both, in the insulin derivative of the formula I, mentioned under (1a).

6. A composition as claimed in claim 5, which contains insulin-B31—Arg—OH or insulin-B31—Arg—Arg—OH.

7. A composition as claimed in claim 1, which contains a plurality of (a) different insulin derivatives of the formula I or (b) different insulins of the formula I or of (a) and (b).

8. A composition as claimed in claim 1, which contains proinsulin or a proinsulin analogue or human C peptide or a combination thereof.

9. A composition as claimed in claim 1, which has a pH between 2.5 and 8.5 and is in the form of a solution or suspension, and contains a conventional isotonicity agent and a conventional preservative.

10. A composition as claimed in claim 1, which additionally contains a conventional buffer substance, if the pH value is between 5.0 and 8.5.

11. A composition as claimed in claim 1, wherein the formulation contains a conventional stabilizer which prevents precipitation of protein on exposure to heat or mechanical stress on contact with various materials.

12. A composition as claimed in claim 1, which contains a suitable amount of zinc, which can be between 0 and 100 μg/100 units.

13. A composition as claimed in claim 1, in which the insulin or proinsulin or des-Phe$^{B1}$-insulin or C peptide or a combination thereof and insulin derivative of the formula I are used in the form of an alkali metal salt or the ammonium salt.

14. A composition as claimed in claim 1, wherein the content of insulin or proinsulin or des-Phe$^{B1}$-insulin or C-peptide or a combination thereof and the content of insulin derivative of the formula I can in each case be, independently of one another, in dissolved, amorphous or crystalline form or a combination thereof.

15. A composition as claimed in claim 1, in which in each case any desired part of the content of insulin or proinsulin or des-Phe-$^{B1}$-insulin or C-peptide or a combination thereof and of the content of insulin derivative of the formula I is in crystalline form, in each case any other desired part of the content of insulin or proinsulin or des-Phe-insulin or C-peptide or a combination thereof and of the content of the insulin derivative of the formula I is in amorphous form, and in each case the remainder of the content of insulin or proinsulin or des-Phe-insulin or C peptide or a combination thereof and of the content of the insulin derivative of the formula I is in dissolved form.

16. A composition as claimed in claim 1, which contains a conventional auxiliary having a delaying action.

17. A composition as claimed in claim 16, in which this delayed action principle is used in combination with the entire active compound content or with parts thereof.

18. A composition as claimed in claim 16, which contains insulin or proinsulin or des-Phe-insulin or C peptide or a combination thereof and insulin derivative of the formula I in combination with a plurality of different auxiliaries having a delaying action.

19. A method of treating a patient suffering from diabetes mellitus which comprises administering an effective amount of an insulin derivative of the formula I and an insulin of the formula I according to claim 1 or a pharmaceutically acceptable salt thereof.

* * * * *